United States Patent [19]
Weimer

[11] Patent Number: 5,593,398
[45] Date of Patent: Jan. 14, 1997

[54] PROTECTIVE UNDERWEAR WITH MALODOROUS FLATUS FILTER

[76] Inventor: Chester L. Weimer, 419 W. 22nd St., Pueblo, Colo. 81003

[21] Appl. No.: 248,766

[22] Filed: May 25, 1994

[51] Int. Cl.$^6$ ........................................... A61F 13/15
[52] U.S. Cl. .................... 604/359; 604/360; 604/395; 2/406
[58] Field of Search .................... 2/406, 408, 53–56; 604/359–361, 395; 450/97–99, 150–153

[56] References Cited

U.S. PATENT DOCUMENTS

| | | | |
|---|---|---|---|
| 2,837,095 | 6/1958 | Stevenson | 604/395 X |
| 3,212,500 | 10/1965 | Bordy | 604/395 |
| 4,182,335 | 1/1980 | Metrullo | 604/377 X |
| 4,718,902 | 1/1988 | Bonito | 604/396 |
| 4,813,950 | 3/1989 | Branch | 604/396 |
| 4,880,417 | 11/1989 | Yabrov et al. | 604/355 |
| 5,207,663 | 5/1993 | McQueen | 604/385.1 |

*Primary Examiner*—Randall L. Green
*Assistant Examiner*—Mark O. Polluta

[57] ABSTRACT

Protective underwear made of air-tight polyurethane-coated nylon (10) with elastic sewn around the waist (12) and around the bifurcated legs (14a, 14b). An exit hole (24) for the flatus is cut from the back, near the bottom, of the underwear. The exit hole is covered with a pocket (16a, 16b) made of porous fabric, and designed in the same shape as the exit hole (24), only larger. The bottom layer of the pocket (16b) is sewn (22) around the edge of the exit hole (24) connecting it to the underwear. The top layer (16a) is sewn (20) around the edge of the bottom layer (16b) and onto the underwear, except at the top, leaving the pocket opening. The pocket opening is kept closed by a fastener. The replaceable filter is large all around than the exit hole (24), but smaller all around than the pocket (16). The top and bottom layers are of wool felt (26a, 26b); and both layers are cut larger than all other layers to facilitate sewing (28). The second layers, on top and bottom, are of polypropylene non-woven fabric (30a, 30b); followed by layers, top and bottom, of fiber glass wool (32a, 32b). In the middle of the filter is a single layer of activated carbon (34).

1 Claim, 5 Drawing Sheets

PROTECTIVE UNDERWEAR WITH MALODOROUS FLATUS FILTER

BACKGROUND OF INVENTION

This invention relates to protective underwear, specifically to the filtering of foul smelling human flatus.

BACKGROUND OF THE INVENTION

Heretofore, the health care industry has provided protective underwear for individuals suffering from urine and feces incontinence. However, for those millions suffering from inflammatory bowel diseases, such as Crohn's disease and ulcerative colitis, no protective underwear are available to filter the malodorous flatus that accompany these diseases.

Some protective underwear are air tight but provide no relief from foul human gas, especially for that segment of the United States population experiencing lactase deficiency or diverticulitis.

OBJECTS AND ADVANTAGES

Accordingly, several objects and advantages were created in this protective underwear. First, the polyurethane coated nylon underwear has elastic around the waist and bifurcated legs, but with a triangular hole cut from the material in the back near the bottom where the anus would normally release the flatus. This triangular hole has rounded corners, and has the purpose of facilitating the exiting of the flatus in a specific area and direction in the otherwise air-tight underwear.

Second, covering the hole from the inside, a pocket is attached to the polyurethane coated nylon close to the edge by needle and thread. This pocket is noticeably larger than the hole and is made of a porous fabric. It is also triangular shaped with rounded corners, and has fasteners of the hook and loop type sewn into the top for easy opening and closing.

Third, a multi-layered gas filter is placed in the pocket. The filter is the same shape, but slightly smaller, then the pocket, and slightly larger than the exit hole. The filter is replaceable and can be removed from the underwear when laundering, or replaced as needed.

And, whereas prior inventions provide for the health problem of incontinence, this invention provides relief from many of the problems associated with Inflammatory Bowel Syndrome (I.B.S.), lactase deficiency, and diverticulitis. Further advantages of my invention will become apparent from a review of the drawings and detailed description.

DESCRIPTION OF THE PREFERRED EMBODIMENTS

Figure 1A:
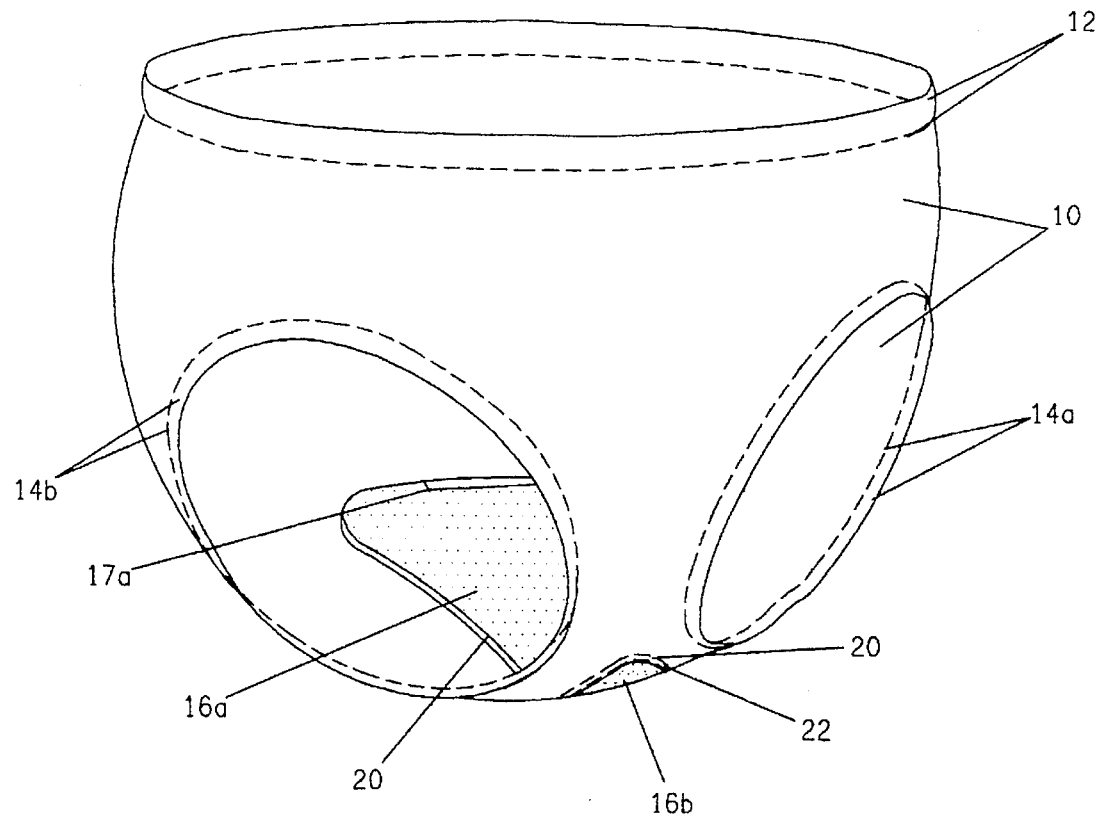
FIGS. 1A and 1B show a perspective view of the protective underwear with the replaceable filter.
Figure 1B:
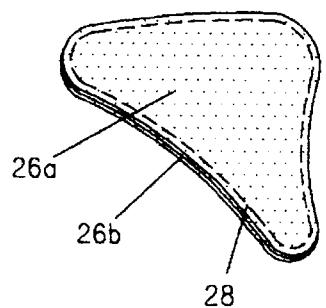

A typical embodiment of the Protective Underwear for Malodorous Flatus is illustrated in FIG. 1A (perspective view) witch the replaceable filter in FIG. 1B. The bifurcated underwear is primarily made of vinyl-coated nylon 10, with a 1 inch elastic band 12 sewn around the waist and a ½ inch elastic band 14 sewn around each of the legs.

Figure 3:
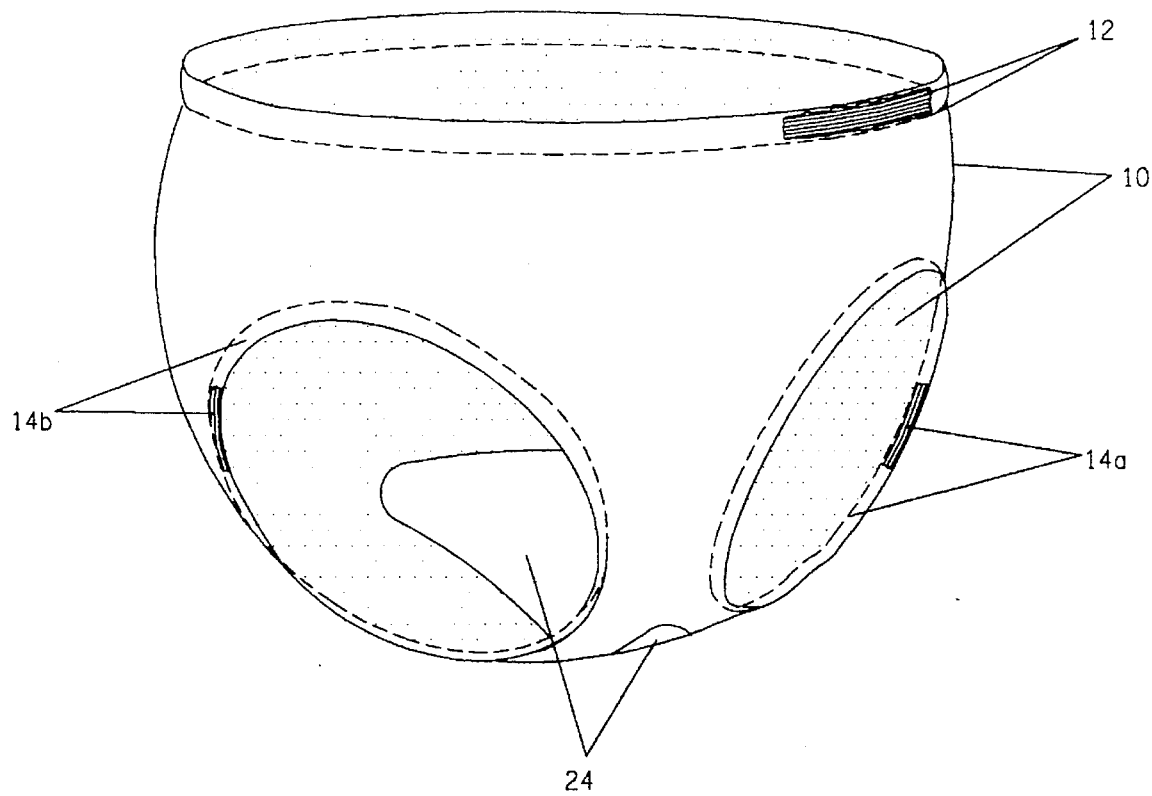
FIG. 3 shows the protective underwear with the exit hole cut out, and the elastic around the waist and bifurcated legs.

As illustrated in FIG. 3, a hole 24 is cut from the underwear at the lower back area where the flatus is normally expelled. The hole is in the shape of a modified triangle with rounded corners. The hole is covered with a pocket 16 shown in FIGS. 4A (perspective view) and 4B (top and bottom layers), shaped larger than the exit hole, and made of porous fabric.

Figure 4A:
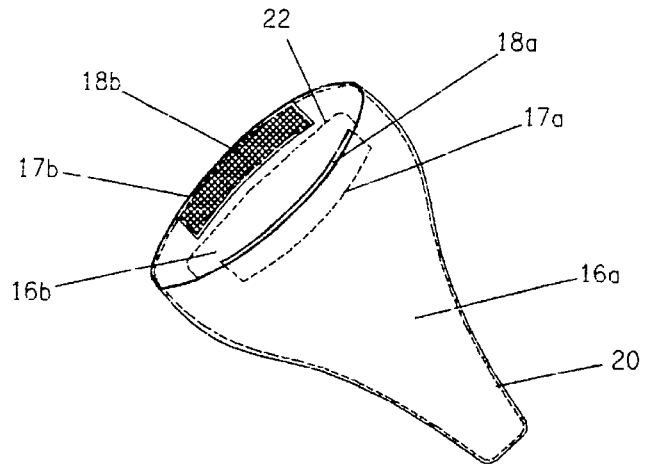
FIGS. 4A and 4B show a perspective view of the pocket with fasteners, and the top and bottom layers of the pocket from the inside view.
Figure 4B:
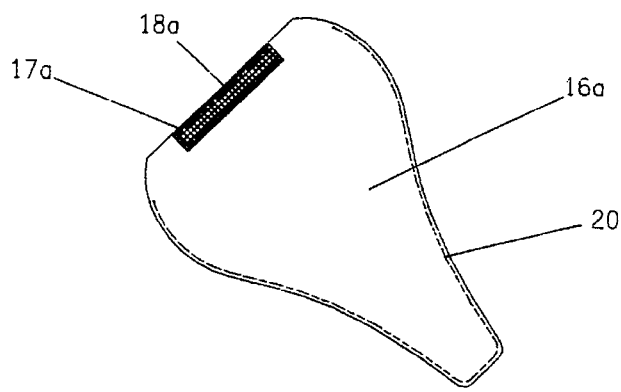
Figure 4B:
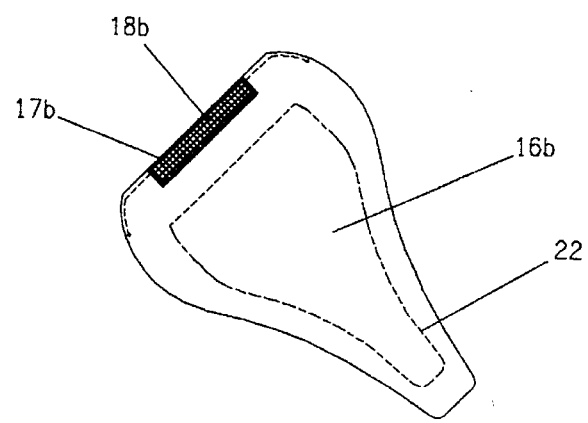

The bottom layer 16b of the pocket is connected to the vinyl-coated nylon 10 at the exit hole 24 by a sewing stitch 22 as seen in FIG. 4B. Also, the bottom layer is attached to the underwear with a stitch 17b connecting a fastener 18b to the bottom layer.

The top layer 16a of the pocket is connected to the bottom layer of the pocket 16b and the vinyl-coated nylon 10 by a sewing stitch 20. Also sewn to the top layer of the pocket, but not connected to the bottom layer or the vinyl-coated nylon, is a fastener 18a connected by a stitch 17a.

Figure 5:
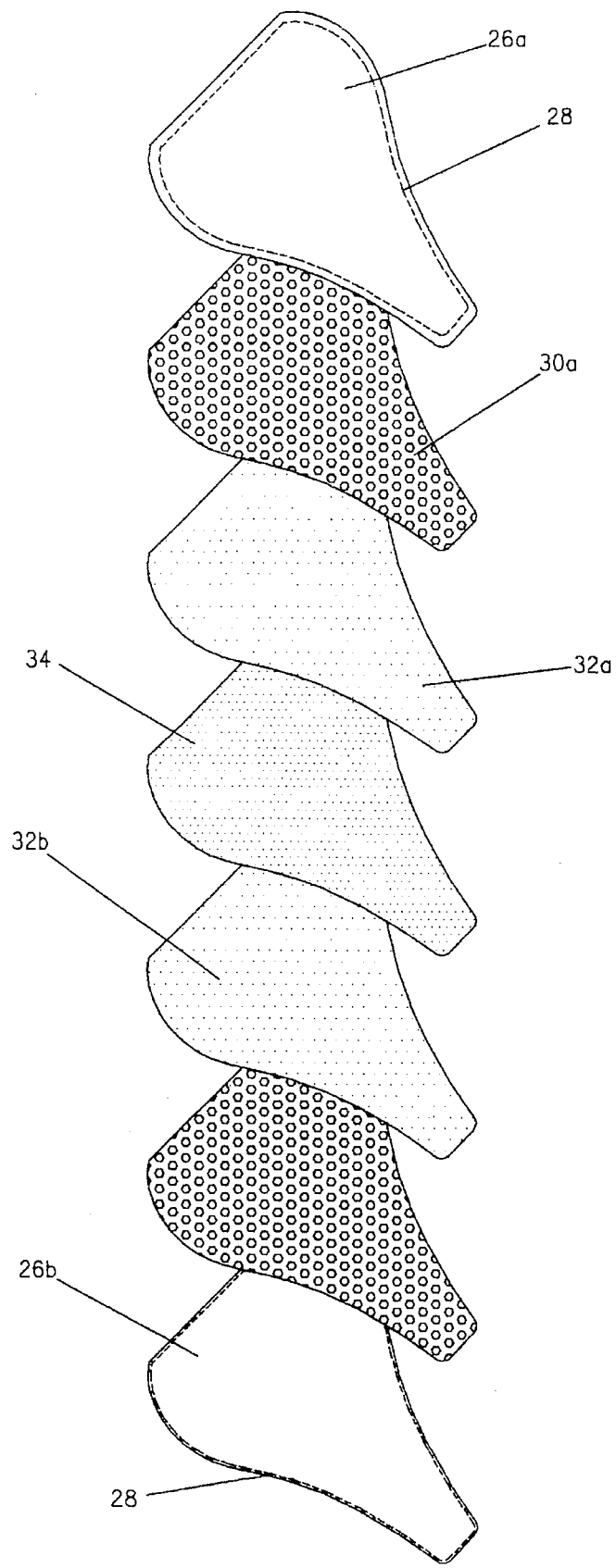
FIG. 5 shows the stratified filter in layers.

FIG. 5 shows the filter in stratified layers, shaped in a size to fit snuggly into the pocket and to be taken out with ease. The top layer of the wool felt 26a and the bottom layer of wool felt 26b are identical in size, which is a ½ inch larger in length and width than the remaining layers. It is made of sheep's wool pressed to ⅛ inch thick felt.

The second layer from the top is made of non-woven, gridded, polypropylene homopolymer 30a and is identical to the second layer from the bottom, which is also polypropylene homopolymer 30b. Both layers are cut ½ inch smaller in length and width than the top layers of wool felt 26a and 26b, and has a thickness of 5 mils.

The third layer from the top is made of fiber glass wool 32a and is identical to the third layer from the bottom, which is also of fiber glass wool 32b. Both layers are cut ½ inch smaller in length and width than the top layers of wool felt 26a and 26b. The layer when sewn into the filter it has a thickness of less than 1/16th of an inch.

At the center of the filter is a single layer of activated charcoal on an open cell foam base 34. It is cut ½ inch smaller in length and width than the top layers of wool felt 26a and 26b. The activated charcoal when sewn into the filter, it has a thickness of ¼ of an inch.

Operation—FIGS. 1 to 5

Figure 2:
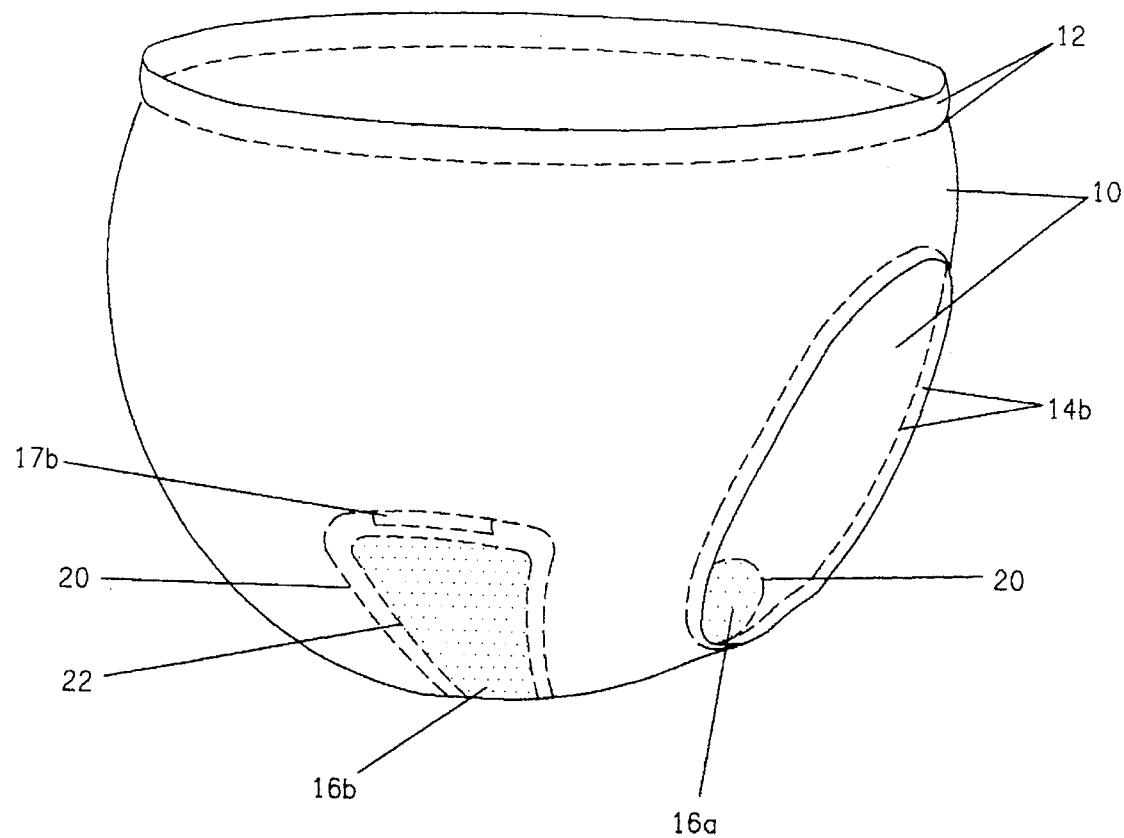
FIG. 2 shows a rear view perspective of the protective underwear.

As shown in FIGS. 1 to 3, the protective underwear for malodorous flatus is made of vinyl-coated nylon 10 with elastic around the waist 12 and bifurcated legs 14. This creates an air-tightness which consequently forces all flatus out through the exit hole 24. The exit hole 24 is covered with a pocket 16 made of any porous fabric, and has a fastener stitched 17 to the top to prevent the filter FIG. 1B and FIG. 5 from slipping out.

The protective underwear can be made of any non-porous material that will allow the flatus to remain inside and eventually out through the exit hole 24. Additionally, the non-porous material used for the underwear may have a polyester or cotton lining in case of sweating.

As seen in FIG. 3, a 1 inch band of elastic 12 is sewn into the waist, and a ½ inch band of elastic 14a and 14b is sewn into each of the legs to aid in the air-tightness of the underwear.

The pocket 16, shown in FIG. 4A and 4B is made of a porous fabric and is ¾ of an inch larger than the exit hole 24 all the way around, except at the top; which is made 1 and a ¼ inch longer to allow material onto which the fastener 18 can be stitched 17. The underwear must be sewn to bottom layer of the pocket with a stitch 22, and stitched 17b again across the top, shown in FIG. 4B, connecting the fastener 18b and the upper portion of the bottom layer to the underwear 10. The top layer 16a of the pocket must be sewn to the bottom layer of the pocket with a stitch 20, to begin ¾ of an inch from the top and continuing around to ¾ of an inch from the top on the other side; connecting the two layers with the underwear 10. An additional stitch 17a is used to connect the fastener 18a to the top of the top layer of the pocket.

The fastener 18 can be of the hook and loop type, or of any for holding the tops of the pocket 16 together. The purpose of the pocket 16 is to hold the filter in place, while the remainder of the underwear maintain air-tightness.

The purpose of the filter, shown in FIG. 1B and 5, is to filter out that 1% of human flatus causing the malodor or bad smell. With each person and on any given day, the malodorous flatus is caused by a variation of 6 substances as a result of undigested fat and protein. They are: skatole, indole, ammonia, volatile amines, hydrogen sulfide, and short-chain fatty acids. To Capture and hold this 1% of malodorous flatus a stratified filter is used.

The top and bottom layers of the filter are of non-woven sheep's wool felt 26, pressed to a ⅛ inch thickness, and are of the type used in respirator filters approved by the Mine Safety and Health Administration and the National Institute for Occupational Safety and Health. They are 95% wool with a 26.2% specific gravity for a density to allow the flatus under expulsion pressure to pass through.

The second layer of the stratified filter is of polypropylene 30a and 30b non-woven fabric with a thickness of 5 mils, a 23.0 cross direction, and a filament count of 57.0. These line pattern nets are used as separation and support media in the filter.

The third layer of the stratified filter is fiber-glass wool 32, composed of 92–95% fibrous glass, 5–8% extended phenol-formaldehyde resin, and 1% non-woven facings. There is no significant odor; it can be with or without non-woven facings, and is cut from a gold to yellow blanket.

In the center of the filter is a single activated carbon filter 34. This activated carbon filter is made from coconut shell material, and has an add-on carbon density of 200% of the base media's weight; resulting in a vast network of microscopic channels for trapping malodorous flatus.

The way this protective underwear for malodorous flatus operates, is to capture the bad smell in the air-tight vinyl-coated nylon 10 in the underwear forcing it out through the exit hole 24. This exit hole 24 is covered with a polyester pocket 16 made larger than the hole, and fitted with a fastener at the top. The pocket 16 is fitted with a filter stratified with wool felt 26, polypropylene, fiberglass wool, and an activated carbon filter 34 in the center designed to filter out the 6 substances causing the malodorous flatus.

Thus, the reader will see that the Protective Underwear With Malodorous Flatus Filter provides a reliable, air-tight, washable underwear which forces the flatus through the specially designed pocket containing a replaceable filter. The very effective filter is layered with various materials to filter out most of the 1% malodorous flatus; yet porous enough to allow the remaining odorless flatus to pass through.

While this invention is primarily designed as an aid to the millions of Americans suffering from Inflammatory Bowel Syndrome, it can be used by all segments of the population seeking to end the social stigma associated with foul smelling human gas. For instance, older adults and senior citizens naturally have a less effective digestive system that comes with aging. This invention could help anyone experiencing a temporary interruption of normal digestion, such as diarrhea or constipation especially when sleeping with their spouse or working with peers. Also, certain races have an intolerance to lactose, and may utilize this invention.

This invention has been described in detail in connection with the preferred embodiments. The preferred embodiments, however, are merely for example only and this invention is not restricted thereto. It will be easily understood by those skilled in the art that variations and modifications can be easily made within the scope of the invention, as defined by the appended claims.

For instance, the bifurcated underwear could be made with drawstrings sewn into the waist and legs as a way to accommodate the various individual sizes while maintaining air-tightness. Also, a pouch can be strategically sewn into the underwear for the purpose of containing a colostomy. This pouch could be sewn into either the front or the back of the underwear to fit the size of the bag and remain air-tight; thereby providing a comfortable and practical way to end the embarrassment associated with malodorous flatus for colostomy users. Also, the underwear can be made with a soft cotton or polyester knit inner lining for maintaining dry skin. And, of course, the underwear and filter can easily be made in various sizes ranging from children to adults, and with a masculine or feminine flair.

The exit hole, pocket, and filter can be made in other sizes and shapes. In addition to smaller or larger sizes, the exit hole, pocket, and filter could be shaped to extend to the front of the underwear to help the filtering process when the user is in a sitting position. Any enlargement of these parts of the invention would help prevent the build-up of moisture.

The filter can be enclosed by a smooth, non-filtering fabric to facilitate the sliding in and out of the pocket. The layers of the filter can also be changed as the state-of-the-art of gas filtering improves. Another variation of the filter would be to add a layer of scented powder or oil to produce a smell favorable to humans. Hence, the filter will not only filter out the malodorous gas, but replace it with a pleasant odor.

In short, this invention can be adapted to fit all sizes and shapes of humans, and can be used either when sleeping or when fully dressed to improve the quality of air we smell.

I claim:

1. A protective underwear comprising:
   a bifurcated vinyl-covered underwear with elastic bands around the waist and legs, a hole in a lower back area of the underwear in the shape of a modified triangle and
   a pocket of porous fabric shaped in a triangle larger than said hole, having a front and back piece sewn onto an edge of said hole leaving an opening with a fastener at the top of said front piece; and
   a filter in the shape of said triangular hole larger than said hole and smaller than said pocket, comprising an outer top and bottom layer of wool felt followed by an inner top and bottom layer of unwoven polypropylene fabric followed by an inner top and bottom layer of fiber glass wool followed by an inner most single layer of activated carbon on an open cell foam base, and sewn together at an edge of said layers.

* * * * *